United States Patent [19]

King

[11] Patent Number: 4,730,617
[45] Date of Patent: Mar. 15, 1988

[54] OBSTETRIC VACUUM EXTRACTOR AND METHOD OF USING THE SAME

[75] Inventor: Siegfried King, Neuried, Fed. Rep. of Germany

[73] Assignee: Herrmann Hepp, Munich, Fed. Rep. of Germany; a part interest

[21] Appl. No.: 894,207

[22] Filed: Aug. 7, 1986

[30] Foreign Application Priority Data

Aug. 7, 1985 [DE] Fed. Rep. of Germany ....... 3528397
Oct. 1, 1985 [DE] Fed. Rep. of Germany ....... 3535055

[51] Int. Cl.⁴ .............................................. A61B 17/42
[52] U.S. Cl. ................................................... 128/352
[58] Field of Search ................ 128/352, 361; 604/176, 604/313–316, 73–75, 115

[56] References Cited

U.S. PATENT DOCUMENTS

| | | | |
|---|---|---|---|
| 2,702,038 | 2/1955 | Uddenberg | 128/361 |
| 3,074,407 | 1/1963 | Moon et al. | 128/310 X |
| 3,120,227 | 2/1964 | Hunter et al. | 128/698 |
| 3,548,830 | 12/1970 | Goey | 604/176 X |
| 3,608,540 | 9/1971 | Sartorius | 604/176 X |
| 3,848,606 | 11/1974 | Chertkoff | 128/352 |

FOREIGN PATENT DOCUMENTS 3138589 4/1983 Fed. Rep. of Germany .

Primary Examiner—Michael H. Thaler
Attorney, Agent, or Firm—Kinney & Lange

[57] ABSTRACT

The invention relates to an obstetric vacuum extractor with a vessel 1 comprising an evacuable vessel chamber open to one side, and to which a pull device 10 is attached. The vessel 1 is divided into at least two vessel chambers 1', 1" open to said one side and evacuable separately.

28 Claims, 5 Drawing Figures

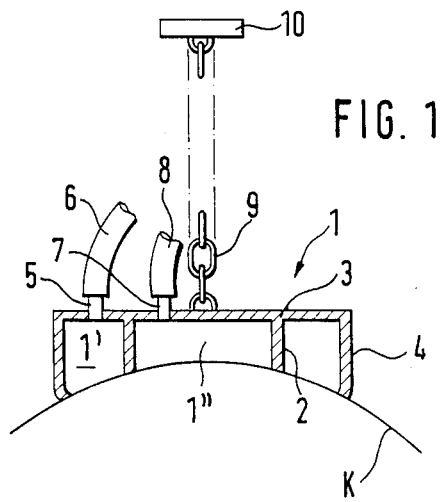
FIG. 1
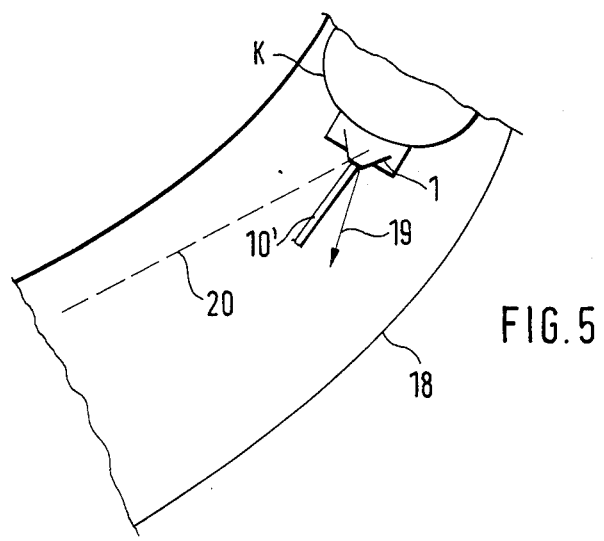
FIG. 2
FIG. 5

OBSTETRIC VACUUM EXTRACTOR AND METHOD OF USING THE SAME

BACKGROUND OF THE INVENTION

1. Field of the Invention

The present invention relates to an obstetric vacuum extractor of the type which has a vessel that has an evacuable vessel chamber open to one side and on which a pulling device is fastened.

2. Description of the Prior Art

Vacuum extraction has been approved for surgical vaginal obstetrics for years. Known devices employed to this end (such as the vacuum extractor known for example from U.S. Pat. No. 2,702,038) consist of an evacuable vessel, the opening of which is applied to the infant's head after introduction into the vagina of a parturient. As a vacuum is created in the vessel, the head adheres to the vessel by suction, with formation of a tissue swelling, so that then through a holding handle and controlled pull movements the birth process can be supported and also accelerated.

However, vacuum extraction, like other instrument delivery aids, are not without risk. At too strong a pull and in particular upon the occurrence of traction forces extending tangentially to the vesel, the vessel adhering to the head of an infant by suction may unintentionally and abruptly detach from the scalp, and this may lead to considerable intracranial pressure fluctuations. For this reason, improvements concerning the handling and the construction of the extractor have been repeatedly proposed.

Thus, for example, from U.S. Pat. No. 2,702,038 (FIG. 6) a vacuum extractor is known where a rigid handle is connected with the vessel via a ball joint to permit better positioning and directing of the vacuum extractor. Such a ball joint, however, does not permit, under traction, a frictionless swiveling of the rigid handle or a free rotation of the head, as a power coupling will occur in the joint. This in turn is what makes the bringing out of the infant's head from the birth canal much more difficult.

Also a vacuum extractor is known in which the force is measured with which the scalp presses against a contact plate disposed in the interior of the vessel during evacuation of the vessel. By the measurement of this pressing force, however, a possible state of danger, in which detachment of the vessel takes place, is not sufficiently predictable, because the pressing force of the scalp is being varied in an entirely unpredictable manner depending on traction forces acting on the vessel from different directions.

The arrangement known from German Patent DE-PS No. 31 38 589 (in which harmful pressure fluctuations upon detachment of the vessel are to be reduced by the fact that a tissue holding device disposed in the interior of the vessel delays a swinging back of the scalp is disadvantageous because with a vessel of such a nature only relatively small traction forces can be transmitted.

It may be said in general that with all known vacuum extractors there is a problem in the sense that the vacuum built up in the vessel collapses abruptly upon exertion of tensile forces (in particular tensile forces not directed coaxially) when in the edge region of the vessel opening a connection is established between the evacuated region and the surrounding. Besides the calculable maximally applicable traction force (which depends on the diameter of the evacuated vessel), such parameters as in particular the direction of pull, the tilting moment and the tissue properties of the head swelling play a decisive role, so that in the final analysis traction and pressure measurements alone cannot indicate reliably enough a threatening detachment, unless in the evaluation of the measurement results a safety zone is taken into account. Taking such a safety zone into consideration, however, would lead to a definite limitation of the employable traction forces.

SUMMARY OF THE INVENTION

The object of the present invention, therefore, is to improve an obstetric vacuum extractor to the effect that a sudden and complete collapse of the vacuum built up in the extractor can be avoided without the need to forgo the optimally employable traction forces.

This problem is solved by a vacuum extractor of the type which has an evacuable vessel chamber open to one side and on which a pulling device is fastened and which is characterized by the fact that its vessel chamber is divided into at least two vessel chambers open to one side, and which can be evacuated separately.

The essential advantage of the present invention consists in that a sudden and abrupt collapse of the vacuum built in the extractor can be avoided, because at least two separately evacuable vessel chambers are provided in the extractor. Preferably there are provided in the extractor two concentrically arranged vessel chambers, which are evacuated through two vacuum pumps. Advantageously, therefore, the birth process to be supported cannot be complicated by an unexpected, abrupt and complete detachment of the extractor from the head of the infant. In case an excessive or a faulty traction is exerted on the outer vessel of the extractor, at first only the narrow, low-dimensioned tissue swelling in the outer chamber can no longer maintain the complete sealing of the vacuum of the outer chamber. Thus the collapse of the vacuum in the outer chamber occurs long before the inner vessel chamber, transmitting the applied traction forces, begins to detach from the produced real tissue swelling. The collapse of the vacuum in the outer chamber (which in a preferred form of realization of the invention is indicated by a signal transmitter) therefore indicates reliably the critical point before the detachment of the inner vessel chamber from the scalp. While the critical point is being indicated, the inner vessel chamber advantageously continues to maintain the connection to the infant's head, until under renewed application of the preferably rigid system to the infant's head the vacuum in the outer vessel chamber is built up again and a renewed labor-synchronized extraction is made possible again.

An essential advantage of a variant of the invention consists in that due to the provision of a central, low cover plate of the vessel chambers the artificial caput succedaneum can be kept relatively flat in the central region of the vessel chambers and therefore can be minimized on the whole, whereas the caput succedaneum in the peripheral region can be built up more in lateral bulges of the vessel chambers and therefore can be optimized. Thereby the power coupling with the infant's head necessary for the extraction can advantageously be intensified. In this manner, without having to forgo the necessary tissue swelling of the suctioned scalp, the infant is traumatized less. Furthermore, the extraction will advantageously be possible earlier, because the necessary tissue swelling requires in all a smaller volume.

The advantage of a variation of the invention, in which the handle is mechanically uncoupled from the vessels in a specific manner, consists in that the infant's head can retain during the birth process its necessary free mobility in the birth canal even under traction, but at the same time, if this is necessary for gentle aid in birth, an active rotation of the infant's head is possible via the preferably rigid holding handle.

Another essential advantage of a preferred form of realization of the vacuum extractor according to the invention (in which the holding or pull handle is connected with the vessel almost without friction via a specific ball bearing joint) consists in that, especially when a non-coaxial pull is exerted through the holding handle, the outer vessel edge executes no tilting movements. Under traction forces acting obliquely or tangentially on the vessel, the balls of the ball bearing joint (which transmit the traction forces from the holding handle to the vessel) are swiveled, and thus the force vectors acting on the vessels change so that less load is applied on the vessel edge which would be normally endangered by detachment due to such an applied traction component. Thereby, advantageously, the danger of detachment will be considerably reduced. Due to the mechanical uncoupling, an almost frictionless rotation of the infant's head during the extraction is advantageously ensured at the same time (besides the traction or pressure movement possible via the holding handle), the head being able to adapt itself optimally to the birth canal situation according to the laws of least resistance, as in a spontaneous birth. According to a variant of the invention, the rotation may be limited to a given range by the provision of appropriate abutment points in the ball bearing joint, so that as needed, if this is desired during the birth process, an active rotation of the little head can be brought about by execution of a rotational movement at the holding handle.

In a further embodiment of the invention, the holding handle is removable from the vessels. The advantage of this is that vessels of different sizes can be applied at the handle. In addition, a simplified sterilization of the vessels of the vacuum extractor is made possible thereby.

In a further advantageous embodiment of the invention, the handle parts of the holding handle are attached pivotably at the handle via a joint, so that when being introduced into the vacuum extractor in the direction of the pull rod of the handle they can be folded in, so as to avoid impediments in handling to the extent possible.

In a further advantageous embodiment of the invention, it is possible during the extraction to pick up the infantile heart actions by a sensor provided centrally in the respective vessel. In the state of the art it is customary, for the determination of heart actions during birth, to apply at the infant's head an appropriate device for the derivation of the heart actions. Such devices must then be removed again before the extractor is applied or, if this is possible, must be applied on the head of the infant anew laterally of the extractor. In the former case this leads to being unable, after the application of the extractor, to determine any internally derived heart actions to be recorded for monitoring the birth process. In the second case, time-consuming steps are necessary for the application of the device laterally of the vessel of the extractor.

In addition, the established contact with the sensor advantageously indicates that there has formed in the respective vessel a sufficiently large tissue swelling allowing the initiation of the extraction.

BRIEF DESCRIPTION OF THE DRAWINGS

In the following, the invention and its variants will be explained more specifically in conjunction with the figures.

FIG. 1 shows a schematic representation of a simple form of realization of the vacuum extractor of the invention;

FIG. 2 shows a further form of realization of the vacuum extractor of the invention;

FIG. 5 illustrates the function of the mechanical uncoupling of a handle from a vacuum extractor according to FIG. 3, applied to the head of the infant, with the head of the infant being in the curved birth canal.

DETAILED DESCRIPTION OF THE PREFERRED EMBODIMENTS

Figure 3:
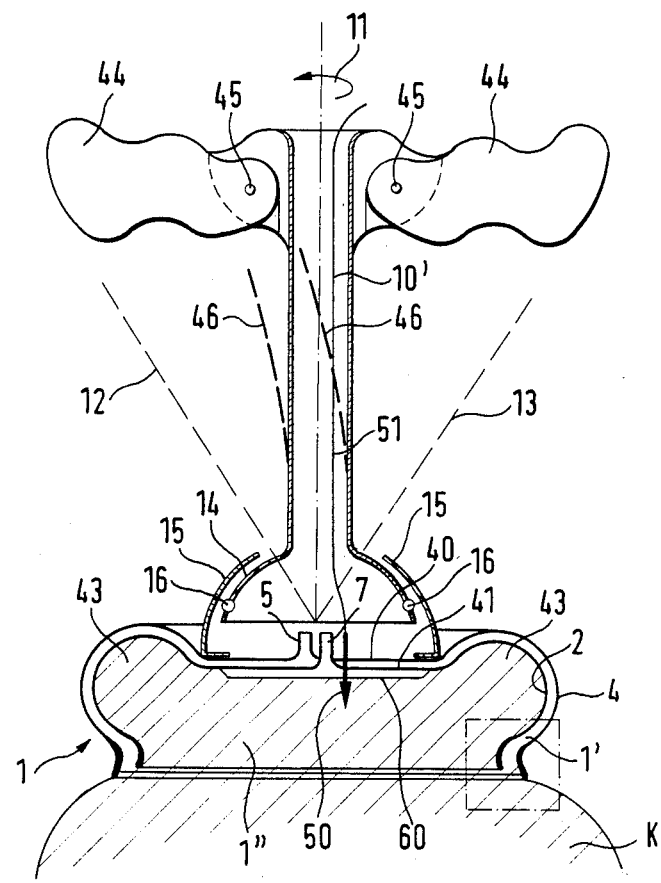
FIGS. 3 and 4 show a further form of realization of the vacuum extractor of the invention, wherein a mechanical uncoupling between the handle and the vessels is provided.

In the schematic representation of FIG. 1, the evacuable vessel of the present vacuum extractor is marked 1. Essentially this vessel consists of an upper wall 3, from which extends downward a preferably annular sidewall 4. In the vessel 1 several, preferably two, vessel chambers 1', 1" are provided, which are preferably arranged concentric to each other. The vessel chambers 1', 1" are separated by an additional annular wall 2 which extends downward from the upper wall 3 and is concentric to the sidewall 4. The outer annular vessel chamber 1' communicates with a suction hose 6 via a suction nipple 5 passed under seal through the upper wall 3. In analogous manner the inner vessel chamber 1" communicates with a suction hose 8 via a suction nipple 7 passed under seal through the upper wall 3. Via the suction hoses 6 and 8, which lead to external vacuum pumps not shown, which may be combined in a vacuum equipment, the vessel chambers 1', 1" can be evacuated separately. Preferably, it is possible to create in the inner vessel chamber 1", which after application of vessel 1 on the head of an infant is located in the region of the fontanelle, a lesser vacuum than in the outer vessel chamber 1', which is not in the region of the fontanelle. For example there are created in the inner vessel chamber 1" a vacuum of 0.8 kp/cm$^2$ and in the outer vessel chamber 1' a vacuum of e.g. 0.99 kp/cm$^2$. Preferably, the suction hoses 6, 8 extend along the chain 9. In place of the chain 9, another pulling device may be provided. The lengths of the annular sidewall 4 and of the annular wall 2 are appropriately dimensioned so that the free ends of the sidewall 4 and wall 2 are, when the vacuum extractor is being applied to the head K of the infant, abutting thereon. This means that the length of the inner wall 2 is, according to the arch of the head, shorter than the length of the outer sidewall 4. When using the vacuum extractor of the invention, only comparatively small tissue swellings form, because the scalp of the infant's head braces additionally against the free end of the inner annular wall 2.

From FIG. 2 a vessel 1 is evident wherein the mobility when working with the vacuum extractor is fully preserved because the two suction nipples 5, 7 are arranged approximately centered or respectively symmetrical to the axis of vessel 1. Details of FIG. 2 which have been explained already in connection with FIG. 1 bear the corresponding reference symbols. The symmetrical arrangement of the suction nipples 5, 7 relative to the longitudinal axis of vessel 1 is possible due to the fact that in the place of the upper wall 3 of the vessel of FIG. 1 a double wall 3', 3" is provided. The individual walls 3', 3" of this double wall are formed one over the other, with a channel between the upper wall 3' and the wall 3' arranged therebelow which connects the suction nipple 5 with the outer vessel chamber 1'. The suction nipple 7, passed under seal through the upper wall 3', leads to the inner vessel chamber 1". Vessel 1 may also be connected for example, to the chain 9 seen in Figure which establishes a connection to a handle 10.

From FIG. 3 is evident a variant of the invention where a pulling or holding handle 10' is mechanically uncoupled from the vessel 1 in such a way that the holding handle 10' can execute a gyratory movement relatve to the vessel 1. Put more precisely, the holding handle 10' is designed so that on the one hand it can rotate relative to the vessel 1 about its longitudinal axis, as is indicated in FIG. 3 by the arrow 11, and that on the other hand it swivels in a given angle region in all directions relative to the longitudinal axis of vessel 1 largely without friction, as is illustrated by the dashed lines 12, 13. The mechanical uncoupling is achieved by the fact that the end of handle 10' toward vessel 1 has an enlarged end 14 which possesses a spherical or ball-shaped outer surface. The vessel 1 has an upward leading, likewise spherical wall 15, which surrounds the spherical outer surface of the enlarged end 14 of the holding handle 10'. At the enlarged end 14 of handle 10' schematically shown ball bearings 16 are provided, by which it is assured that the spherical outer surfaces of the enlarged end 14 can roll off or slide on the spherical surface 15. Put more precisely, the ball bearings 16 permit the enlarged end 14 and the holding handle 10' connected therewith to rotate relative to vessel 1 about the longitudinal axis of vessel 1 and at the same time to pivot relative to the longitudinal axis, as has already been mentioned above. For example, the holding handle 10' can be pivoted with respect to the longitudinal axis of vessel 1 about an angle of 30° or more in all directions. To reduce injuries in the execution of gyratory movements which can result through wedging in of maternal tissue parts, a preferably rubber-like sleeve (not shown) may be arranged over the region in which the upper end region of wall 15 and the enlarged end 14 overlap. This sleeve does not hinder the gyratory movement.

In the illustrated form of the vacuum extractor of the present invention, the holding handle 10' is preferably hollow, so that the hoses connected with the draw-off nipples 5, 7 (not shown) can be passed through the holding handle 10'.

Figure 4:
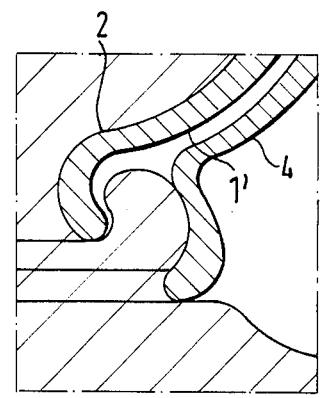

From the representation of FIG. 3 it is evident also that according to a variant of the invention the distance between the wall 2 and sidewall 4 can be chosen relatively small, so that the inner vessel chamber 1" performs practically all of the holding functions and that the scalp sucked into the outer vessel chamber 1' (see enlarged representation of FIG. 4) is used for the purpose of serving, in the manner explained more fully below, as indicator for the threatening detachment of the inner vessel chamber 1" from the scalp of the infant's head. After the application of the previously explained vessel of the vacuum extractor of FIG. 3 on the scalp K of the infant's head, the two vessel chambers 1' and 1" are evacuated. In so doing (for instance in the manner visible from FIG. 4 in which the scalp is shown hatched diagonally), a part of the scalp is sucked into the outer vessel chamber 1'. Now if during the extraction traction forces are exerted on the vessel, before the breaking off of the vacuum in the inner vessel chamber 1" the case always reliably occurs that the small tissue swelling (which before the exertion of the critical pull brings about a complete sealing of the outer vessel chamber 1') is deformed in the outer vessel chamber in such a way that a connection is established between the vacuum of the outer vessel chamber 1' and the surrounding. In this case, the inner vessel chamber 1" is however still securely and firmly sucked on to the head of the infant, but the vacuum in the outer vessel chamber 1' collapses. By a suitable signal transmitter this state is indicated to the obstetrician, so that long before the inner vessel chamber 1" starts to detach from the produced actual head swelling he can take measures which lead to the build-up of the vacuum in the outer vessel chamber 1' again. This means that by the reduction of the vacuum in the outer, comparatively small-volume chamber 1', it is reliably indicated that a situation has arisen in which with a further increase of the traction force exerted on the scalp K through the inner vessel chamber 1" a detachment of the vacuum extractor is imminent. By suitable dimensioning of the form of the edge region of the opening of the outer vessel chamber 1' and of the distance from each other of the sidewalls 4 and wall 2 forming the outer vessel chamber 1' it is possible to bring about in good time and reliably a timely signal transmission before the detachment of the extractor also in dependence on the vacuum applied in the outer vessel chamber 1'.

In this connection it is of special importance that until the moment of the breaking off of the vacuum in the outer vessel chamber 1' the necessary maximum traction can still be exerted via the inner vessel chamber 1" due to the previously mentioned dimensioning.

With reference to FIG. 5, which shows a head K of an infant present in the birth canal 18, there will now be explained more fully the mode of operation of the mechanically uncoupled vacuum extractor of FIG. 3. First the extractor is introduced into the birth canal 18 in such a way that the free ends of the wall 2 and sidewall 4 of the vessel chambers 1' and 1" apply against the head K of the infant. Via the suction hoses extending through the holding handle 10' and the end region 14, the vessel chambers 1' and 1" are now evacuated separately. At that, the entire vessel 1 attaches itself to the infant's head by suction. Via the holding handle 10' and the enlarged end 14 traction/pressure forces can now be exerted on the head K of the infant, to pull or to guide the infant's head through the birth canal 18. It is of essential importance in this connection that by the mechanical uncoupling between vessel 1 and handle 10' of the vacuum extractor it can be achieved by suitable pushing at the holding handle 10' that there is always exerted on the vessel 1 a force vector 19 which extends approximately perpendicular to the head of the infant. It is thereby achieved that tilting of vessel 1 relative to the surface of the infant3 s head K is greatly reduced and that at least the vacuum built up in the inner vessel chamber 1" does not break off. The broken line 20 in FIG. 5 indicates how the vector of the traction force on the vessel 1 extends in the known vacuum extractor. It is readily evident that the tensile stresses extending along line 20 may cause the vessel 1 in FIG. 5 to be lifted off the head K on its right side, as the tensile stress is predominantly not along the axis of vessel 1. By means of the present extractor it can be achieved by suitable exertion of pressure via the rigid holding handle 10' that the angle between the longitudinal axes of handle 10' and of vessel 1 of the extractor is always such, in dependence on the curvature of the birth canal 18, that the traction forces acting on the vessel 1 (which are brought about by pulling and pushing and the holding handle 10') extend approximately perpendicular to the head surface of the infant. At the same time the head can execute the natural and necessary rotation movements, because due to the mechanical uncoupling with respect to the holding handle 10', the vessel 1 can rotate freely.

Preferably, there is provided at a suitable point a sensor (not shown) which, by measuring the air-liter output of the vacuum pump for the outer vessel 1' upon breakoff of the vacuum in the outer vessel chamber 1', produces a signal for a control unit (not shown), which in turn excites an appropriately acoustic signal transmitter which indicates to the physician that measures must be taken that will lead to reestablishment of the vacuum in the outer vessel chamber 1'.

In the following discussion, another embodiment of the invention will be explained in connection with FIG. 3. For the sufficient adhesion of the extractor the formation of a caput succedaneum is necessary. The extraction should therefore not be begun before a sufficient "head swelling formation" is achieved, which substantially fills the inner vessel of the extractor. In the form of the vacuum extractor of the present invention of FIG. 3, a sufficient formation of the caput succedaneum can be detected by the fact that a mandrel arrangement is provided, comprising, at least one pin 50, which preferably comprises a tip or point and is electrically conductive, which is preferably arranged in the central region of the inner vessel chamber 1'' in such a way that it extends a given distance in the direction of the open end of the vessel chamber 1''. The pin 50 is fastened in the upper vessel wall 3'' of the inner vessel chamber 1'' or respectively in the plate 60. Upon development of the caput succedaneum, the pin 50 is pressed a few millimeters into the sucked-up infantile scalp. As soon as this has happened, the prerequisites for a labor-synchronized extraction should exist. The pin 50 is connectable with an external measuring device via a schematically represented electric line 51 extending through the holding handle 10'. As soon as the pin 50 digs into the infantile scalp, heart actions are observable through the measuring device during the entire extraction operation.

The above described pin 50 can be used also in connection with conventional extractors which have only one chamber.

The devices marked with the reference symbol 60 in the figures involve support plates known in themselves, on which upon formation of the vacuum in the extractor the infant's head takes support. Provision is thereby made that the suction nipple 7 is not closed.

In a further variant of the invention the central region of the two vessel chambers is sunk inwardly, so that the tissue swelling is built up faster in a small volume, owing to which the extraction can be initiated earlier. Besides, as it develops, the tissue swelling expands into the annular bulge 43 of the vessel chambers leading from the low plate 40, 41 in said central region outward, so that, by way of the tissue swelling produced over the circumference of the opening of the inner vessel chamber 1'' in the region projecting laterally outward, an optimum connection is established between the tissue swelling as a whole and the vacuum extractor.

In the manner also evident from Figure 3, the handle parts 44 fastened on the pull rod of the holding handle 10' of the vacuum extractor may be connected with the pull rod of the handle via joints 45, so that when introducing the vacuum extractor into the vagina they can be folded in the direction of the pull rod, so as not to be in the way. After introduction, the handle parts 44 are unfolded into the position shown in FIG. 3, in which the applied traction forces can be transmitted through them to the pull rod.

It is conceivable to form the pull rod of the holding handle 10', not of a completely rigid tube, but of a semi-rigid tube, so that it can be bent during the extraction process for example into the position shown by the lines 46 in FIG. 3. It is achieved thereby that the holding handle 10' can be pivoted in a still greater angle than the angle shown by way of example, which becomes possible through the ball joint arrangement; this may be advantageous in particular for an infant's head standing very high in the birth canal.

Lastly, it is conceivable also to design the ball joint arrangement so that the balls 16 thereof are held, not in the end region 14 as shown in FIG. 3, but in the wall 15.

What is claimed is:

1. An obstetric vacuum extractor for aiding fetal passage through the birth canal has a vessel which comprises an evacuable vessel chamber open to one side, and on which a pulling device is fastened, characterized in that the vessel (1) is divided into at least two vessel chambers (1', 1'') open to one side, which can be evacuated separately.

2. An extractor according to claim 1, characterized in that the vessel (1) is divided into two vessel chambers (1', 1'') by a wall (2).

3. An extractor according to claim 2, characterized in that for the formation of an inner vessel chamber (1'') and an outer vessel chamber (1') concentric thereto the vessel (1) is subdivided by an annular wall (2).

4. An extractor according to claim 3, characterized in that the vessel (1) consists of an upper wall (3) and of a sidewall (4) integrally formed therein, and that the wall (2) is integrally formed on the upper wall (3) in the interior of the vessel (1).

5. An extractor according to claim 4, characterized in that the wall (2) and the sidewall (4) have essentially the form of hollow circular cylinders.

6. An extractor according to claim 4, characterized in that a lower free end of sidewall (4), in accordance with the form of a head (K) of an infant, is farther removed from the upper wall (3) than a lower free end of the wall (2).

7. An extractor according to claim 4, characterized in that extending through the upper wall (3) is a suction nipple (5) to the outer vessel chamber (1') and an additional suction nipple (7) to the inner vessel chamber (1'').

8. An extractor according to claim 4, characterized in that the upper wall (3) is divided into a first upper wall (3') and a second upper wall (3'') spaced therefrom which extends partially below the first upper wall (3'), that the wall (2) is integrally formed on the second wall (3''), that the sidewall (4) is integrally formed on the first wall (3'), that a first suction nipple (5) is integrally formed on the first wall (3') and establishes via the interspace between the first wall (3') and the second wall (3") a connection to the first vessel chamber (1'), and that a second suction nipple (7) is connected with the second wall (3"), establishes a connection to the second vessel chamber (1") and is passed under seal through the first wall (3').

9. An extractor according to claim 8, characterized in that the first suction nipple (5) and the second suction nipple (7) are arranged close together and symmetrical to the longitudinal axis of the vessel (1).

10. An extractor according to claim 8, characterized in that the second suction nipple (7) is adjacent to the first suction nipple (5) and is held spaced from it, and that at least the longitudinal axis of the first suction nipple (5) extends along the longitudinal axis of the vessel (1).

11. An extractor according to claim 4 characterized in that the distance between the wall (2) and the sidewall (4) is dimensioned so and the form of the regions continguous to the aperture edges of the wall (2) and of the sidewall (4) is constituted so that in dependence on the vacuum in the outer vessel chamber (1') the scalp of an infant's head (K) is introduced into the aperture region thereof in such a way that the vacuum in the outer vessel chamber (1') is reduced by establishment of a connection to the surrounding before the inner vessel chamber (1") begins to detach from the scalp of the head (K) introduced into it due to the vacuum created therein, and that upon reduction of the vacuum in the outer vessel chamber (1') a warning signal is producible.

12. An extractor according to claim 4, characterized in that a central region of the upper wall (3) is sunk in the direction of the vessel chamber openings.

13. An extractor according to claim 4, characterized in that the vessel consists of a first upper wall (3') and of a sidewall (4) integrally formed thereon, that a second upper wall (3") is spaced from the first upper wall (3') and extends partially below the first upper wall (3'), that a wall (2) is integrally formed on the second wall (3") to subdivide the vessel (1) into its two vessel chambers (1', 1"), and that a central region of the upper walls (3', 3") is sunk in the direction of the vessel chamber openings.

14. An extractor according to claim 1, characterized in that the vessel (1) is connected with a holding handle (10) via a chain (9) integrally formed on it in the center thereof.

15. An extractor according to claim 1, characterized in that the vessel (1) is connected with a holding handle (10') comprising a pull rod, which handle is mechanically coupled to the vessel (1) in such a way that relative to the vessel (1) it can execute a gyratory movement and is rotatable about its longitudinal axis.

16. An extractor according to claim 15, characterized in that the end of the pull rod of the holding handle (10') toward the vessel (1) has an enlarged end (14) with a spherical outer surface, that the upper wall (3') of the vessel has a generally spherical wall (15) extending from the vessel (1) toward the holding handle (10') and which surrounds the spherical outer surface of the enlarged end (14) of the holding handle (10'), that between the enlarged end (14) of the holding handle (10') and the end region of the wall (15) surrounding it a ball bearing arrangement (16) is provided in such a way that an inner face of the wall (15) can roll off or slide on the spherical outer surface of the enlarged end (14), and that an upper end of the end region of the wall (15) is dimensioned so that the enlarged end (14) of the holding handle (10') is held in it.

17. An extractor according to claim 16, characterized in that the ball bearing arrangement (16) is fastened at the enlarged end (14).

18. An extractor according to claim 16, characterized in that the holding handle (10') has a longitudinal bore through which extend hoses connecting the first suction nipple (5) and the second suction nipple (7) with a vacuum equipment.

19. An extractor according to claim 15 characterized in that the pull rod of the holding handle (13) is a semi-rigid tube.

20. An extractor according to claim 15, characterized in that on the pull rod of the holding handle (10') pull handle parts foldable in the direction of the pull rod are arranged.

21. An extractor according to claim 1, characterized in that a probe arrangement (50) is provided which upon the creation of a vacuum in the vessel (1) is pushed a given distance into the infant's scalp, and that the probe arrangement (50) is connectable with a measuring device for the determination of heart actions.

22. An extractor according to claim 21, characterized in that the probe arrangement (50) protrudes into the inner vessel chamber (1").

23. An extractor according to claim 21, characterized in that the probe arrangement (50) consists of at least one pin.

24. An extractor according to claim 1, characterized in that a probe arrangement (50) is provided which upon the creation of a vacuum in the vessel (1) is pushed a given distance into the infant's scalp, that the probe arrangement (50) is connectable with a measuring device for the determination of heart actions, and that the probe arrangement (50) is connectable with the measuring device via an electric line (51) which extends through the longitudinal bore of the holding handle (10').

25. In a fetal extractor having a bell-shaped chamber designed for mounting an open side thereof on the head of a fetus, means for creating a vacuum within said chamber to affix the extractor to the fetal head, and means for pulling on said chamber to facilitate movement of the fetus through the birth canal, the improvement which comprises:
a second chamber having an open side which is designed for mounting on the head of a fetus and which surrounds the open side of the bell-shaped chamber when the extractor is mounted on the fetal head, and means for separately creating a vacuum in the second chamber to affix the extractor to the fetal head.

26. A method of extracting a fetus from a birth canal comprises the steps of:
(a) positioning a fetal extractor having at least two evacuable chambers, open to the same side with that open side against the head of the fetus;
(b) separately creating a vacuum in each of the chambers to draw the extractor and fetus into a coupled relation; and
(c) exerting a force on the extractor to facilitate movement of the fetus coupled thereto through the birth canal.

27. The method of claim 26 wherein the open side of an outer one of the evacuable chambers surrounds the open side of an inner one of the evacuable chambers.

28. The method of claim 27, and further comprising the step of:
creating a greater vacuum in the inner chamber than in the outer chamber.

* * * * *